(12) United States Patent
Kiyose

(10) Patent No.: US 9,818,929 B2
(45) Date of Patent: Nov. 14, 2017

(54) ULTRASONIC DEVICE, METHOD FOR MANUFACTURING THE SAME, ELECTRONIC DEVICE AND ULTRASONIC IMAGING DEVICE

(71) Applicant: SEIKO EPSON CORPORATION, Tokyo (JP)

(72) Inventor: Kanechika Kiyose, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 541 days.

(21) Appl. No.: 14/541,528

(22) Filed: Nov. 14, 2014

(65) Prior Publication Data

US 2015/0141827 A1    May 21, 2015

(30) Foreign Application Priority Data

Nov. 20, 2013   (JP) ................... 2013-240276

(51) Int. Cl.
```
H01L 41/08      (2006.01)
H01L 41/33      (2013.01)
H01L 41/053     (2006.01)
A61B 8/00       (2006.01)
B06B 1/06       (2006.01)
```
(52) U.S. Cl.
CPC ............ *H01L 41/33* (2013.01); *A61B 8/4427* (2013.01); *A61B 8/4483* (2013.01); *A61B 8/4494* (2013.01); *B06B 1/064* (2013.01); *H01L 41/053* (2013.01); *Y10T 29/42* (2015.01)

(58) Field of Classification Search
CPC ..... H01L 41/33; H01L 41/053; A61B 8/4427; A61B 8/4483; A61B 8/4494; B06B 1/064
USPC .................................................. 310/322, 334
See application file for complete search history.

(56) References Cited

U.S. PATENT DOCUMENTS

| | | |
|---|---|---|
| 2002/0089395 A1 | 7/2002 | Ella et al. |
| 2006/0043843 A1 | 3/2006 | Sugiura et al. |
| 2007/0040477 A1 | 2/2007 | Sugiura et al. |
| 2008/0116765 A1 | 5/2008 | Sugiura et al. |
| 2010/0277040 A1 | 11/2010 | Klee et al. |
| 2013/0338502 A1* | 12/2013 | Onishi ............... A61B 8/4494 600/443 |
| 2016/0033454 A1* | 2/2016 | Matsuda ........... G01N 29/2437 73/632 |

(Continued)

FOREIGN PATENT DOCUMENTS

| | | |
|---|---|---|
| JP | 2002-268645 A | 9/2002 |
| JP | 2006-094459 A | 4/2006 |

(Continued)

*Primary Examiner* — Thomas Dougherty
(74) *Attorney, Agent, or Firm* — Global IP Counselors, LLP

(57) ABSTRACT

An ultrasonic device includes a substrate having a first opening, a second opening and a wall part partitioning the first opening and the second opening; a first vibration film and a second vibration film which close the first opening and the second opening respectively; a first piezoelectric element and a second piezoelectric element which are formed on surfaces of the first vibration film and the second vibration film opposite to the substrate; an acoustic matching layer which is disposed within the first opening and the second opening so as to come into contact with the first vibration film and the second vibration film.

12 Claims, 10 Drawing Sheets

(56) References Cited

U.S. PATENT DOCUMENTS

2016/0035963 A1\* 2/2016 Kurokawa ........... A61B 8/4483
367/7

FOREIGN PATENT DOCUMENTS

| JP | 2010-539442 A | 12/2010 |
| JP | 2011-259274 A | 12/2011 |

\* cited by examiner

ULTRASONIC DEVICE, METHOD FOR MANUFACTURING THE SAME, ELECTRONIC DEVICE AND ULTRASONIC IMAGING DEVICE

BACKGROUND

1. Technical Field

The present invention relates to an ultrasonic device and a manufacturing method thereof, as well as a probe, an electronic device and an ultrasonic imaging device which utilize the same.

2. Related Art

An ultrasonic device utilizing a vibrating thin film is well known. For example, a piezoelectric element is formed on a surface of the vibration film of a silicon oxide or a silicon nitride, as described in JP-T-2010-539442. A structural body is disposed to surround the piezoelectric element on the surface of the vibration film. A rear surface of the vibration film is arranged to face a target object. As a result, an ultrasonic wave is transmitted from the rear surface of the vibration film.

JP-T-2010-539442 is an example of related art.

In JP-T-2010-539442, for formation of the piezoelectric element, the rear surface of the vibration film is supported on a surface of a substrate. Subsequent to the formation of the piezoelectric element, the substrate is removed by etching. The rear surface of the vibration film is formed to have a planar surface. When intervening between the vibration film and the target object, an acoustic matching layer and an acoustic coupling layer cause crosstalk between the vibration films adjacent to each other.

An ultrasonic device is desired that can effectively prevent crosstalk between vibration films arranged adjacent to each other.

SUMMARY (1) An aspect of the invention refers to an ultrasonic device that is provided with a substrate, a first vibration film, a second vibration film, a first piezoelectric element, a second piezoelectric element, and an acoustic matching layer, wherein the substrate has a first opening, a second opening and a wall part partitioning the first opening and the second opening, wherein the first vibration film and the second vibration film respectively close the first opening and the second opening, wherein the first piezoelectric element and the second piezoelectric element are respectively formed on surfaces of the first vibration film and the second vibration film opposite to the substrate, and wherein the acoustic matching layer is disposed within the first opening and the second opening so as to be in contact with the first vibration film and the second vibration film.

The wall part partitions the acoustic matching layer. The acoustic matching layer adjacent to the first vibration film and the acoustic matching layer adjacent to the second vibration film are partitioned with the wall part. With this configuration, it is possible to prevent crosstalk of the ultrasonic wave propagated through the acoustic matching layer.

(2) A plurality of the first openings may be arranged in a row, and a plurality of the second openings may be arranged in a row parallel to the arrangement of the first openings. According this aspect, it is possible to connect the first piezoelectric elements arranged in a row commonly to electrodes in correspondence with the first openings arranged in a row. Similarly, it is possible to connect the second piezoelectric elements arranged in a row commonly to electrodes in correspondence with the second openings arranged in a row. In this configuration, it is possible to operate the arranged first piezoelectric elements simultaneously, and to operate the arranged second piezoelectric elements simultaneously. Thereby, it is possible to prevent crosstalk of the ultrasonic wave transmitting through the acoustic matching layer between the first piezoelectric element group and the second piezoelectric element group.

(3) The wall part may have a first wall part with a first height in a thickness direction of the substrate, and a second wall part with a second height larger than the first height. In this way, it is possible to provide the first wall part and the second wall part with individual functions.

(4) The ultrasonic wave device may be further provided with an acoustic lens which is in contact with the second wall part and coupled to the acoustic matching layer. According to this aspect, the acoustic matching layer is coupled to the acoustic lens for use of the ultrasonic device. The acoustic lens allows ultrasonic wave vibrations transmitted from the first vibration film and the second vibration film to converge at a focus position. The acoustic lens is positioned at the second wall part in relation to the first vibration film and the second vibration film. In this way, the thickness of the acoustic matching layer is determined by the distance between the acoustic lens and the first vibration film/the second vibration film. It is possible to control the thickness of the acoustic matching layer with the height of the second wall part. It is possible to set an optimum thickness for the transmission of ultrasonic wave. Besides, the acoustic matching layer can be prevented from deforming even when being pressed to an object to be detected, as much as possible. It is possible to maintain the acoustic matching layer.

(5) The acoustic matching layer may be disposed between the acoustic lens and the first wall part. According to this aspect, the acoustic matching layer contributes to an adhesion between the acoustic lens and the first wall part. Accordingly, it is possible to suppress the decrease in an adhesion area between the acoustic matching layer and the acoustic lens, regardless of the disposition of the wall part, as much as possible. It is possible to stabilize the connection between the acoustic lens and the acoustic matching layer.

(6) The ultrasonic device may be provided with an exterior frame which surrounds the first opening and the second opening consecutively in a plan view viewed from the thickness direction of the substrate and has a height larger than the wall part in relation to the thickness direction of the substrate. According to this aspect, it is possible to inject a raw material of the acoustic matching layer as a fluid into the first opening and the second opening for the formation of the acoustic matching layer. Besides, the exterior frame can block the raw material flowing from the first opening and the second opening. In this configuration, it is possible to securely inject the raw material into all of the first openings and the second openings.

(7) The first vibration film may have a first resonance frequency, and the second vibration film may have a second resonance frequency different from the first resonance frequency. The vibration film exhibits the maximum sensitivity for the ultrasonic wave in a band region of the resonance frequency. Accordingly, it is possible to receive the ultrasonic wave in band regions varying depending on the vibration films. In this configuration, it is possible to detect a harmonic component of the transmitting frequency, or expand the received band region of the ultrasonic wave.

(8) The acoustic matching layer may have the same thickness at the first opening and the second opening. Ordinarily, the thickness of the acoustic matching layer corresponds to an odd multiple of a quarter of a wavelength of ultrasonic wave. Accordingly, it is possible to achieve acoustic matching even when the same thickness is set at the first opening and the second opening in case a harmonic relationship is satisfied between the first resonance frequency and the second resonance frequency.

(9) The acoustic matching layer may have different thicknesses at the first opening and the second opening. Ordinarily, the thickness of the acoustic matching layer corresponds to an odd multiple of a quarter of a wavelength of ultrasonic wave. The thickness of the acoustic matching layer can be optimized for each of the first openings and the second openings.

(10) The ultrasonic device can be assembled into a probe to be utilized. In this instance, the probe can be provided with the ultrasonic device and a housing supporting the ultrasonic device.

(11) The ultrasonic device can be assembled into an electronic device to be utilized. In this instance, the electronic device is connected to the ultrasonic device and a processing device which is connected to the ultrasonic device and processes the output of the ultrasonic device.

(12) The ultrasonic device can be assembled into an ultrasonic imaging device to be utilized. In this instance, the ultrasonic device can be provided with the ultrasonic device and a display device for displaying an image created from the output of the ultrasonic device.

(13) Another aspect of the invention refers to a method for manufacturing an ultrasonic device, which includes forming a first piezoelectric element and a second piezoelectric element on a surface of a film material of a substrate which has the film material on a first surface; forming a first opening and a second opening which are mutually partitioned with a wall part from a second surface on a rear side with respect to the first surface of the substrate, and forming a first vibration film supporting the first piezoelectric element and a second vibration film supporting the second piezoelectric element on the film material; injecting a fluid raw material of an acoustic matching layer into the first opening and the second opening; and covering the injected fluid with an acoustic lens and curing the fluid body to attach the acoustic lens.

In the manufactured ultrasonic device, the wall part partitions the acoustic matching layer. The acoustic matching layer in contact with the first vibration film and the acoustic matching layer in contact with the second vibration film are separated from each other with the wall part. In this way, it is possible to prevent crosstalk of the ultrasonic wave transmitting through the acoustic matching layer. For the formation of the acoustic matching layer, the fluid of the raw material can be simply injected within the first opening and the second opening, making it possible to simplify the manufacturing process. The acoustic matching layer can be securely adhered to the first vibration film, the second vibration film and the acoustic lens.

(14) The wall part may have a first wall part with a first height in a thickness direction of the substrate and a second wall part with a second height larger than the first height. According to this aspect, the acoustic lens comes into contact with the second wall part. The acoustic lens is positioned at the second wall part in relation to the first vibration film and the second vibration film. In this instance, the acoustic matching layer can be intervened between the acoustic lens and the first wall part. The acoustic matching layer can contributes to the adhesion between the acoustic lens and the first wall part.

(15) For the formation of the first opening and the second opening, the film material can be formed at the planar surface with the first vibration film having a first film thickness and the second vibration film having a second film thickness. According to this aspect, the injected fluid is allowed to extend so as to be planar surface. Accordingly, the fluid has different thicknesses at a part corresponding to the first vibration film and a part corresponding to the second vibration film. In this way, it is possible to control the thickness of the acoustic matching layer.

BRIEF DESCRIPTION OF THE DRAWINGS

The invention will be described with reference to the accompanying drawings, wherein like numbers reference like elements.

DESCRIPTION OF EXEMPLARY EMBODIMENTS

The following describes an embodiment of the invention with reference to the attached drawings. The embodiments explained below are not intended to limit improperly the contents of the invention described in claims. None of the structural details explained in the embodiments are absolutely necessary for the solution of the invention.

(1) Overall Structure of an Ultrasonic Diagnosis Device

Figure 1:
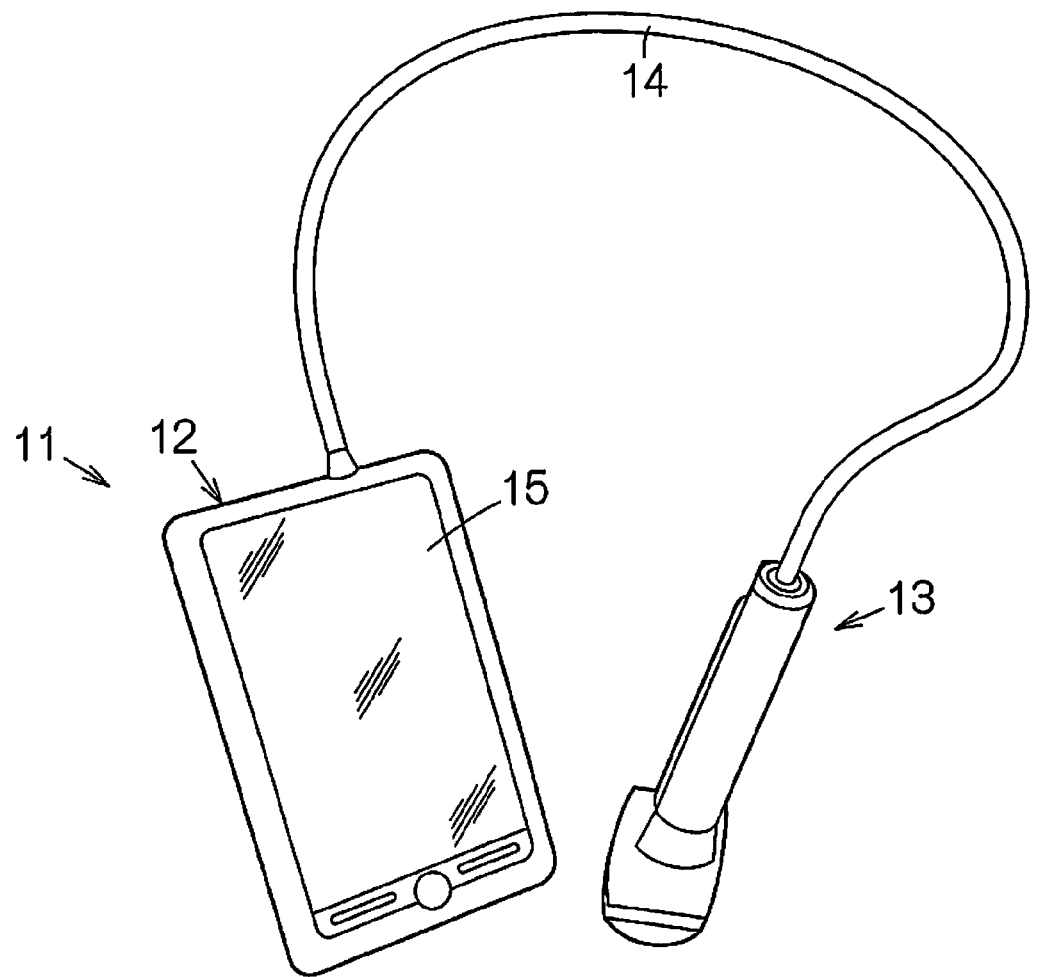
FIG. 1 is an external view schematically showing one specific example of an electronic device, namely an ultrasonic diagnosis device.

FIG. 1 schematically shows one specific example of an electronic device, namely an ultrasonic diagnosis device (ultrasonic imaging device) 11. The ultrasonic diagnosis device 11 is provided with a device terminal (processing device) 12 and an ultrasonic probe (probe) 13. The device terminal 12 and the ultrasonic probe 13 are connected to each other via a cable 14. Electric signals are transmitted through the cable 14 between the device terminal 12 and the ultrasonic probe 13. A display panel (display device) 15 is assembled into the device terminal 12. A screen of the display panel 15 is exposed at a surface of the device terminal 12. In the device terminal 12, an image is created on the basis of ultrasonic waves detected with the ultrasonic probe 13. An imaged detection result is displayed on the screen of the display panel 15.

Figure 2:
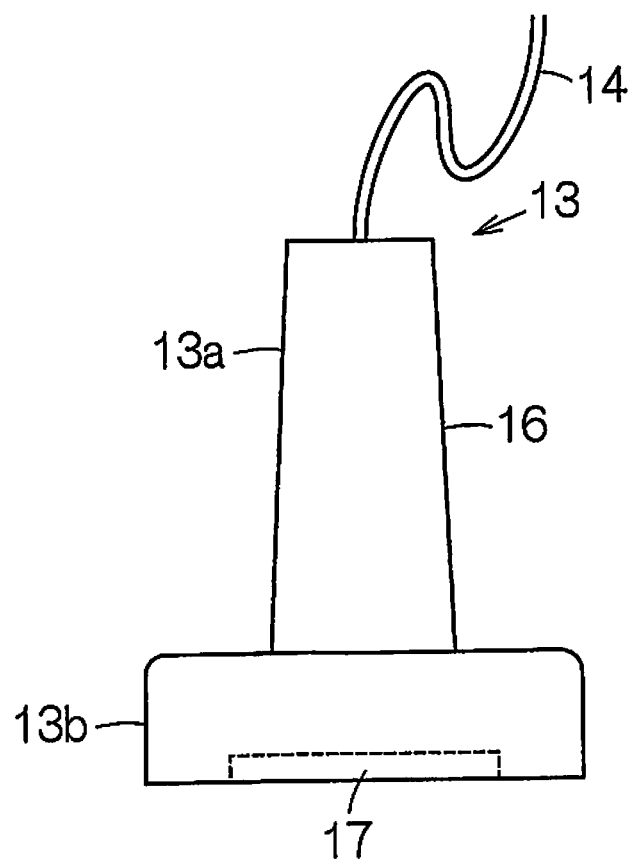
FIG. 2 is an expanded front view of an ultrasonic probe.

As shown in FIG. 2, the ultrasonic probe 13 has a housing 16. An ultrasonic device 17 is accommodated within the housing 16. A surface of the ultrasonic device 17 can be exposed at a surface of the housing 16. The ultrasonic device 17 outputs the ultrasonic wave from the surface and receives a reflection wave of the ultrasonic wave. Moreover, the ultrasonic wave 13 can be provided with a probe head 13b detachably connected to a probe main body 13a. In this case, the ultrasonic device 17 can be assembled within the housing 16 of the probe head 13b.

(2) Configuration of the Ultrasonic Device According to First Embodiment

Figure 3:
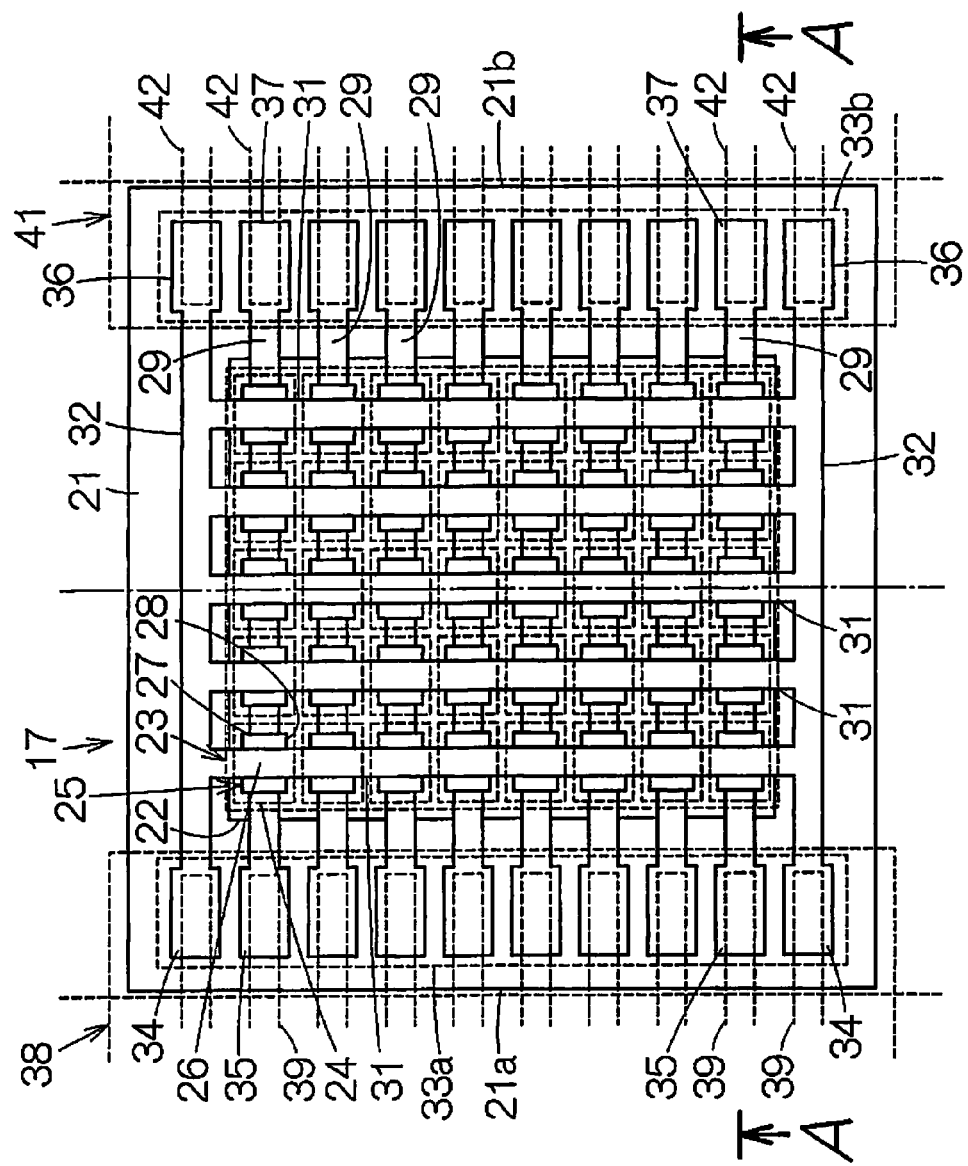
FIG. 3 is an expanded plan view of an ultrasonic device according to the first embodiment.

FIG. 3 schematically shows a plan view of the ultrasonic device 17 according to the first embodiment. The ultrasonic device 17 is provided with a base 21. An element array 22 is provided on the base 21. The array 22 is constituted by an arrangement of ultrasound transducer elements (hereinafter referred to as "elements") 23. The arrangement is in form of a matrix (an array) with a plurality of lines and a plurality of rows. The arrangement may also be established as a zigzag arrangement. In such a zigzag arrangement, a group of elements 23 in an even row can be displaced with respect to a group of elements 23 in an odd row by one half of a line pitch. One of the number of the elements in an odd row and the number of the elements in an even row may be lower than the other by one.

Each element 23 is provided with a vibration film 24. The vibration films 24 will be explained below in detail. In FIG. 3, the contour of each vibration film 24 is depicted as a dotted line in a plan view in a direction perpendicular to a film surface of the vibration film 24 (a plan view in a thickness direction of a substrate). A piezoelectric element 25 is formed on the vibration film 24. In the piezoelectric element 25, a piezoelectric film 28 is interposed between a top electrode 26 and a bottom electrode 27, as described below. These are layered one above the other. The supersonic device 17 is formed as a single ultrasonic transducer element chip.

A plurality of first electric conductors 29 is formed on the surface of the base 21. The first electric conductors 29 extend in parallel to each other in a row direction of the arrangement. One first electric conductor 29 is assigned to each row of elements 23. One first electric conductor 29 is disposed commonly to (i.e. shared by) the elements 23 arranged in a row direction of the arrangement. The first electric conductor 29 forms the bottom electrode 27 for each of the elements 23. For example, a laminate of titanium (Ti), iridium (Ir), platinum (Pt) and titanium (Ti) can be utilized for the first electric conductor 29. It is also possible to use another electric conductor as the first electric conductor 29.

A plurality of second electric conductors 31 is formed on the surface of the base 21. The second electric conductors 31 extend in parallel to each other in a row direction of the arrangement. One second electric conductor 31 is assigned to each line of the elements 23. One second electric conductor 31 is disposed commonly to the elements 23 arranged in the line direction of the arrangement. The second electric conductor 31 forms the top electrode 26 for each element 23. The second electric conductors 31 are connected at both ends to a pair of extension wires 32. The extension wires 32 extend in parallel to each other in the row direction of the arrangement. Accordingly, all of the second electric conductors 31 have the same length. In this configuration, the top electrodes 26 are connected commonly to the elements 23 of the overall matrix. The second electric conductor 31 can be made of iridium (Ir), for example. It is also possible to use another electric conductor as the second electric conductor 31.

It is possible to switch the electrical connection of the elements 23 for each row. In response to the switch of the electrical connection, it is possible to achieve a linear scan and a sector scan. Since the elements 23 in a single row can output ultrasonic waves simultaneously, the number of single lines, that is, the number of lines of the arrangement can be set depending on the output level of the ultrasonic wave. The number of lines can be set in a range of 10 to 15, for example. In figure, some lines are not shown, and five lines are shown. The number of rows of the arrangement can be set depending on the extent of a scan range. The number of rows can be set to 128 or 256, for example. In the figures, some rows are not shown, and only eight rows are shown. The functions of the top electrode 26 and the bottom electrode 27 can be reversed. That is, the bottom electrodes can be connected commonly to the elements 23 of overall matrix, while the top electrodes can be connected commonly to each row of the arrangement.

The contour of the base 21 has a first side 21a and a second side 21b, which are defined by a pair of mutually parallel lines and face each other. A first terminal array 33a is disposed as a single line between the first side 21a and a contour of the element array 22. A line of a second terminal array 33b is disposed as a single line between the second side 21b and a contour of the element array 22. The first terminal array 33a can form one line parallel to the first side 21a. The second terminal array 33b can form one line parallel to the second side 21b. The first terminal array 33a is constituted by a pair of top electrode terminals 34 and a plurality of bottom electrode terminals 35. Similarly, the second terminal array 33b is constituted by a pair of top electrode terminals 36 and a plurality of bottom terminals 37. The two ends of each one extension wire 32 are respectively connected to the top electrode terminals 34, 36. The extension wire 32 and the top electrodes 34, 36 can be formed plane-symmetrically in relation to a perpendicular plane bisecting the element array 22. The two ends of one second electric conductor 31 are respectively connected to the bottom electrode terminals 35, 37. The second electric conductor 31 and the bottom electrodes 35, 37 can be formed plane-symmetrically in relation to a perpendicular plane bisecting the element array 22. Herein, the contour of the base 21 has a rectangular shape. The contour of the base 21 may also be square or trapezoidal.

A first flexible printed circuit board (hereinafter referred to as "first circuit board") 38 is connected to the base 21. The first circuit board 38 covers the first terminal array 33a. The first circuit board 38 is provided at its one end with electrically conductive lines, namely first signal lines 39 that respectively correspond to the top electrode terminals 34 and the bottom electrode terminals 35. The first signal lines 39 are respectively connected so as to face the top electrode terminals 34 and the bottom electrode terminals 35. Similarly, a second flexible printed circuit board (hereinafter referred to as "second circuit board") 41 covers the base 21. The second circuit board 41 covers the second terminal array 33b. The second circuit board 41 is provided at its one end with electrically conductive lines, namely second signal lines 42 that respectively correspond to the top electrode terminals 36 and the bottom electrode terminals 37. The second signal lines 42 are respectively connected so as to face the top electrode terminals 36 and the bottom electrode terminals 37.

Figure 4:
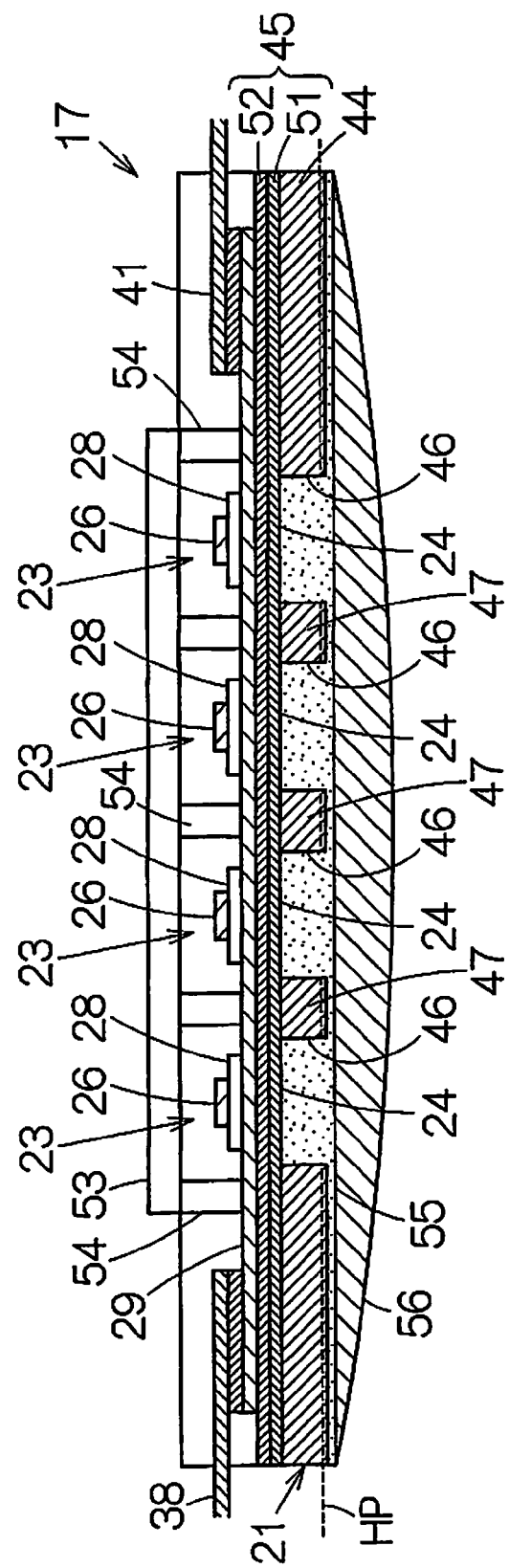
FIG. 4 is a cross-sectional view along A-A line in FIG. 3.

As shown in FIG. 4, the base 21 is provided with a base plate 44 and a flexible film 45. The flexible film 45 is formed over the entire surface of the base plate 44. The base plate 44 is made of silicon (Si), for example. The base plate 44 is provided with an opening 46 for each element 23. The openings 46 are disposed in array form in relation to the base plate 44. A contour of a region in which the openings 46 are disposed corresponds to a contour of the element array 22. A partitioning wall 47 is disposed between two openings adjacent to each other. A wall thickness of the partitioning wall 47 corresponds to an interval between the openings 46. The partitioning wall 47 defines two wall surfaces within planes which extend in parallel to each other. The wall thickness corresponds to a distance between the two wall surfaces. That is, the wall thickness can be defined by a length of a normal line which is orthogonal to the wall surfaces and interposed between the wall surfaces.

The flexible film 45 is made of a silicon oxide ($SiO_2$) layer 51 layered on a surface of the base plate 44 and a zirconium oxide ($ZrO_2$) layer 52 layered on a surface of the silicon oxide layer 51. The flexible film 45 closes the openings 46. In this configuration, a portion of the flexible film 45 forms the vibration film 24, corresponding to the contour of the opening 46. The vibration film 24 is that portion of the flexible film 45 that is exposed through the opening 46, and that is capable of vibrating in the thickness direction of the base plate 44. The film thickness of the silicon oxide 51 can be set in accordance with the resonance frequency.

The first electric conductor 29, the piezoelectric film 28 and the second electric conductor 31 are layered in this order on a surface of the vibration film 24. The piezoelectric film 28 can be made of lead zirconate titanate (PZT), for example. It is also possible to use another piezoelectric material as the piezoelectric film 28. The piezoelectric film 28 covers at least a portion of the bottom electrode 27 and a portion of the vibration film 24. The top electrode 26 covers at least a portion of the piezoelectric film 28. Herein, the piezoelectric film 28 covers the surface of the first electric conductor 29 completely under the second electric conductor 31. With the function of the piezoelectric film 28, it is possible to prevent short-circuits between the first electric conductor 29 and the second electric conductor 31.

A backing material 53 is attached on the flexible film 45 on a surface of the base plate 44. The backing material 53 forms voids between the backing material 53 and the surface of the flexible film 45. The piezoelectric elements 25 are disposed within these voids. The backing material 53 is supported on a surface of the flexible film 45 by a wall material 54. The wall material 54 maintains an interval between the backing material 53 and the surface of the flexible film 45. The wall material 54 is supported with the base material 44 on an exterior side of a contour of the openings 46.

An acoustic matching layer 55 is layered on a rear surface on a rear side of the surface of the base plate 44. The acoustic matching layer 55 covers the rear surface of the base plate 44 while also being disposed within the openings 46. The acoustic matching layer 55 comes into contact with the vibration film 24 within the openings 46. The acoustic matching layer 55 is adhered intimately to the vibration film 24 without forming any voids. For example, a silicone resin film can be used for the acoustic matching layer 55. The partitioning walls 47 have a larger acoustic impedance than the acoustic matching layer 55.

An acoustic lens 56 is layered on the acoustic matching layer 55. The acoustic lens 56 is adhered intimately to a surface of the acoustic matching layer 55 without forming any voids. The exterior surface of the acoustic lens is formed into a partially cylindrical surface. The partially cylindrical surface has an apex line that is parallel to the second electric conductors 31. A curvature of the partially cylindrical surface is set in accordance with a focus position of the ultrasonic wave transmitted from the row of elements 23 connected to one of the second electric conductors 31. The acoustic lens 56 can be made of a silicone resin, for example.

(2) Operation of the Ultrasonic Diagnosis Device

Next, the operation of the ultrasonic diagnosis device will be briefly explained. For the transmission of ultrasonic waves, a pulse signal is supplied to the piezoelectric elements 25. The pulse signal is supplied to the elements 23 in each row through the bottom electrode terminals 35, 37 and the top electrode terminals 34, 36. An electric field acts on the piezoelectric film 28 between the bottom electrode 27 and the top electrode 26 at each element 23. The piezoelectric film 28 vibrates in response to the ultrasonic wave. The vibration of the piezoelectric film 28 is transmitted to the vibration film 24. In this way, the vibration film 24 performs ultrasonic vibration. The ultrasonic vibration of the vibration film 24 is transmitted within the acoustic matching layer 55. The ultrasonic vibration is transmitted to the acoustic lens 56 to be emitted therefrom. As a result, a desired ultrasonic beam is transmitted towards on object (for example, the interior of a human body).

The reflection wave of the ultrasonic wave is transmitted to the acoustic lens 56 and the acoustic matching layer 55 so as to vibrate the vibration film 24. The ultrasonic vibration of the vibration film 24 allows the piezoelectric film 28 to perform ultrasonic vibration at the desired frequency. An electric voltage is output from the piezoelectric elements 25 in response to piezoelectric effect of the piezoelectric elements 25. An electric potential is generated between the top electrode 26 and the bottom electrode 27 at each element 23. The electric potential is output as an electric signal from the bottom electrode terminals 35, 37 and the top electrode terminals 34, 36, enabling the detection of the ultrasonic wave.

The ultrasonic wave is repetitively transmitted and received. As a result, a linear scan and a sector scan are achieved. After completion of the scan, an image is created on the basis of a digital output signal. The created image is displayed on a screen of the display panel 15.

Ordinarily, the ultrasonic probe 13 is pressed to an object to be detected for the formation of the ultrasonic image. In this way, a fluid acoustic coupling material intervenes between the object to be detected and the acoustic lens 56. For example, water can be utilized for the acoustic coupling material. The function of the acoustic coupling material assures an acoustic matching between the object to be detected and the acoustic lens 56, making it possible to prevent an ultrasonic reflection at an interface. The wire pattern and so on, such as the piezoelectric elements 25, the first electric conductors 29 and the second electric conductors 31 are disposed on a front side of the base 21, allowing the piezoelectric elements 25 and the wire pattern to be separated by the flexible film 45 from the acoustic coupling material. With this configuration, it is possible to protect the piezoelectric elements 25 and the wire pattern from water. Accordingly, a moisture-proof material should be used for the flexible film 45.

For the ultrasonic wave transmission, the vibration film 24 performs ultrasonic vibration. The ultrasonic vibration is transmitted within the acoustic matching layer 55 so as to be transmitted from the interface of the acoustic matching layer 55. The ultrasonic vibration is transmitted to the acoustic lens 56 through the interface. In this configuration, the acoustic matching layer 55 is partitioned with the partitioning walls 47 arranged between adjacent vibration films 24. The acoustic matching layer 55, which is in contact with each vibration film 24, is divided with the partitioning walls 47. Interfaces are generated acoustically between adjacent acoustic matching layers 55, due to the difference in the acoustic impedance between the acoustic matching layers 55 and the partitioning walls 47. The interfaces prevent ultrasonic transmission. The ultrasonic crosstalk is prevented during the ultrasonic vibration of a single vibration film 24. If the partitioning walls 47 were not formed and the acoustic matching layer 55 were to extend commonly for all the elements 23, then the ultrasonic vibration transmitted from one element 23 would be reflected from the interface between the acoustic matching layer 55 and the acoustic lens 56, and propagated to the vibration films 24 of other elements 23.

In the ultrasonic device 17, a group of elements 23 in one row is connected commonly to the same first electric conductor 29. The electrodes can be connected commonly to the piezoelectric elements 25 in one row, in correspondence with the openings 46. The rows of the openings 46 are arranged in parallel. The piezoelectric elements 25 of each row can operate simultaneously. The partitioning walls 47 are formed at least between adjacent openings 46 of different rows, making it possible to prevent crosstalk of the ultrasonic wave propagated through the acoustic matching layer 55 between a group of the piezoelectric elements 25 in one row and a group of the piezoelectric elements 25 in an adjacent row.

(3) Method for Manufacturing the Ultrasonic Device

Figure 5:
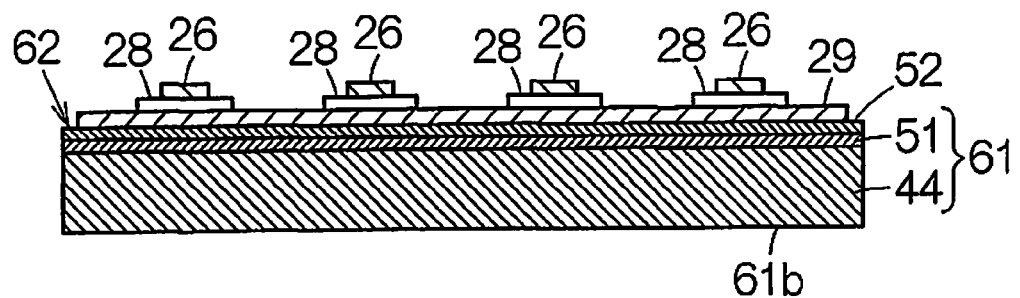
FIG. 5 is an expanded cross-sectional view schematically showing how a piezoelectric element is formed in a method for manufacturing an ultrasonic device.

Next, a method for manufacturing the ultrasonic device 17 will be briefly explained. As shown in FIG. 5, a substrate 61 is prepared. The substrate 61 is made of silicon, for example. The surface of the substrate 61 is subjected to thermal treatment to be provided with an oxide film. Silicon of the substrate 61 is oxidized to be formed into silicon oxide. The oxide film has a uniform film thickness. In this way, the substrate 44 and the silicon oxide layer 51 are formed from the substrate 61. A zirconium layer 52 is formed over the entire surface of the silicon oxide layer 51, and can be formed by sputtering, for example. The zirconium film is formed to have a uniform film thickness. The zirconium film is subjected to oxidization treatment. In this way, the zirconium oxide layer 52 is formed to have a uniform film thickness. The laminate of the silicon oxide layer 51 and the zirconium oxide layer 52 establishes a film material 62. The film material 62 corresponds to the flexible film 45.

Subsequently, the piezoelectric elements 25 are formed on the surface of the film material 62. For example, a raw material layer of an electrically conductive material is formed over the entire surface of the zirconium oxide layer 52, and can be formed by sputtering, for example. The raw material layer is formed to have a uniform film thickness. A pattern of photoresist is formed on the surface of the raw material layer. The pattern is formed into the shape of the first electric conductor 29. Etching treatment is performed from the surface of the raw material layer. As a result, the first electric conductor 29 is formed from the raw material layer. Similarly, the piezoelectric film 28 and the top electrode 26 (second electric conductor 31) are formed on the surface of the film material 62.

Figure 6:
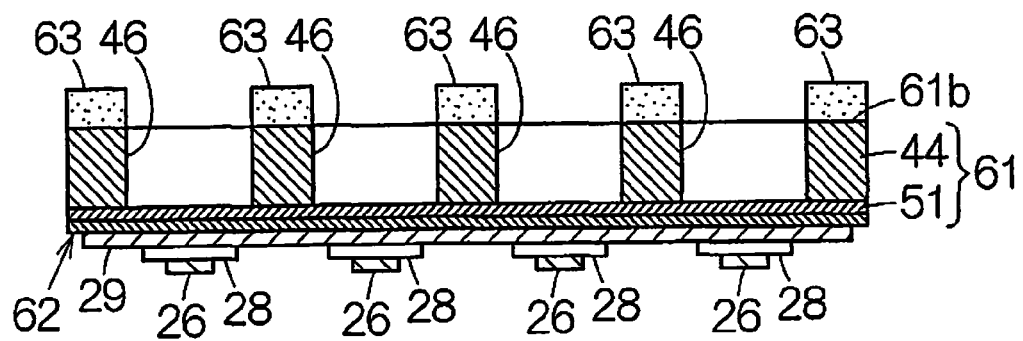
FIG. 6 is an expanded cross-sectional view schematically showing a step of forming an opening in the method for manufacturing the ultrasonic device.

In this way, after the first electric conductor 29, the second electric conductor 31, the top electrode terminals 34, 36 and the bottom electrode terminals 35, 37 are formed in addition to the piezoelectric elements 25, as shown in FIG. 6, the openings 46 are formed in the substrate 44 from the rear surface (second surface) of the substrate 61. For the formation, the substrate 44 is subjected to etching treatment from the rear side. A pattern of the photoresist 63 is formed on the rear surface 61b of the substrate 61. The pattern is shaped into the contour of the openings 46. With the etching treatment, the rear surface 61b of the substrate 61 is etched away at the locations outside the photoresist 63. In this way, the silicon oxide layer 51 acts as an etching stop layer. As a result, the film material 62 establishes the vibration film 24 at the opening 46.

Figure 7:
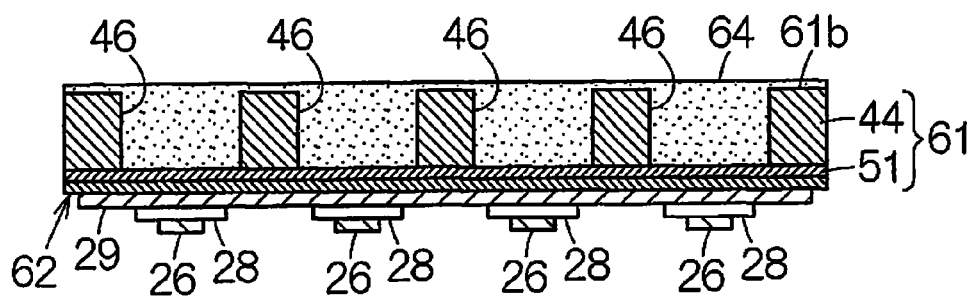
FIG. 7 is an expanded cross-sectional view schematically showing a step of injecting a material of an acoustic matching layer in the method for manufacturing the ultrasonic device.

Subsequently, as shown in FIG. 7, a fluid raw material 64 of the acoustic matching layer 55 is injected into the openings 46. The raw material 64 has fluidity, and fills the voids within the openings 46. The raw material 64 comes into complete contact with the vibration film 24 sufficiently. In this situation, the fluid raw material 64 extends evenly on the rear surface 61b of the substrate 61. A planar surface of the raw material 64 extends in a single plane at the rear surface 61b of the substrate 61.

Figure 8:
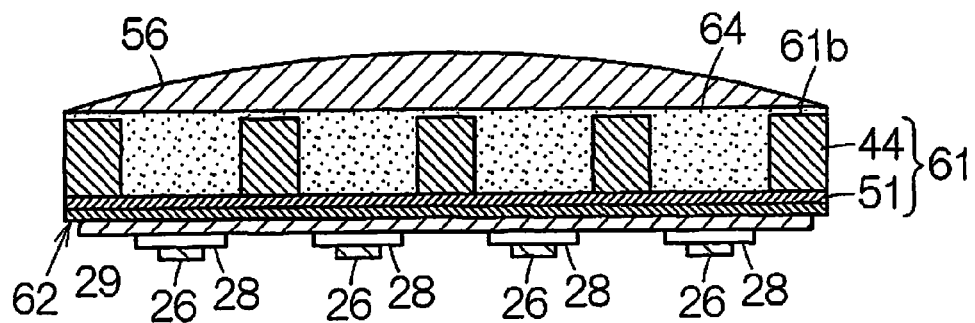
FIG. 8 is an expanded cross-sectional view schematically showing a step of adhering an acoustic lens in the method for manufacturing the ultrasonic device.

As shown in FIG. 8, the injected fluid raw material 64 is covered with the acoustic lens 56. The raw material 64 has fluidity and comes into complete contact with the acoustic lens 56. Subsequently, the fluid is cured. With the curing of the fluid, the acoustic matching layer 55 is established. The acoustic lens 56 adheres to the acoustic matching layer 55. The acoustic matching layer 55 is securely adhered intimately to the vibration film 24 and the lens 56. According to the adhesion, secure ultrasonic transmission is established.

Subsequently, the first circuit board 38 and the second circuit board 41 are connected to the substrate 44. After the first circuit board 38 and the second circuit board 41 are mounted, a backing material 53 is connected to the surface of the substrate 61. In this way, the ultrasonic device 17 is manufactured.

(4) Configuration of Ultrasonic Device According to Second Embodiment

Figure 9:
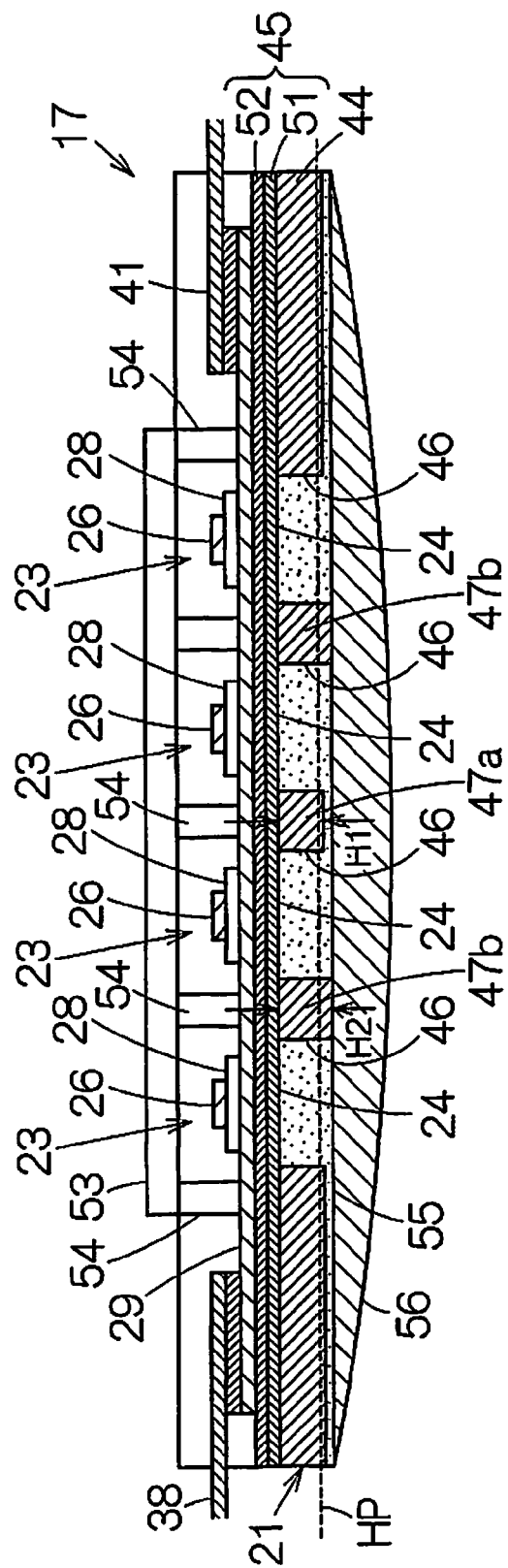
FIG. 9 is an expanded cross-sectional view corresponding to FIG. 4 according to a second embodiment of the ultrasonic device.

FIG. 9 schematically shows a cross-sectional view of the ultrasonic device 17a according to the second embodiment. In the ultrasonic device 17a, the partitioning walls 47 include a first wall 47a with a first height H1 in a thickness direction of the substrate 47 and a second wall 47b with a second height H2. The second height H2 is larger than the first height H1. The first height H1 and the second height H2 can be measured from the rear surface of the silicon oxide layer 51 in a direction that is orthogonal to the surface of the flexible film 45. Herein, the first height H1 and the second height H2 correspond to the thickness of the substrate 44. The acoustic lens 56 comes into contact with a top surface of the second wall 47b. The acoustic matching layer 55 is disposed between the acoustic lens 56 and the first wall 47a. With respect to other aspects, the ultrasonic device 17a has the same configuration as that according to the first embodiment.

In the ultrasonic device 17a, the acoustic lens 56 is positioned at the second wall 47b in relation to the vibration film 24. In this way, the thickness of the acoustic matching layer 55 is set by the distance between the acoustic lens 56 and the vibration film 24. The thickness of the acoustic matching layer 55 can be controlled by the height of the second wall 47b. The optimum thickness for ultrasonic transmission can thus be set. Besides, even when the acoustic lens 56 is pressed to the object to be detected, the acoustic matching layer 55 can be kept from deforming as much as possible. The thickness of the acoustic matching layer 55 can be maintained.

As mentioned above, the acoustic matching layer 55 functions as an adhesive for the acoustic lens 56. The acoustic matching layer 55 is interposed between the first wall 47a and the acoustic lens 56, thereby contributing to adhesion of the acoustic lens 56 and the first wall 47a. Regardless of the position of the partitioning walls 47, it is possible to restrict the reduction of the adhesion area between the acoustic matching layer 55 and the acoustic lens 56 to a minimum. It is possible to stabilize the coupling of the acoustic lens 56 to the acoustic matching layer 55.

For fabrication of the ultrasonic device 17a, the rear surface 61b of the substrate 61 is subjected to etching treatment in the formation of the openings 46. In this way, when the etching treatment can be suppressed at a portion corresponding to the second wall 47b, it is possible to establish the second height H2 of the second wall 47b. When being adhered, the acoustic lens 56 is pressed to the top surface of the second wall 47b. The second wall 47b positions the acoustic lens 56.

(5) Configuration of Ultrasonic Device According to Third Embodiment

Figure 10:
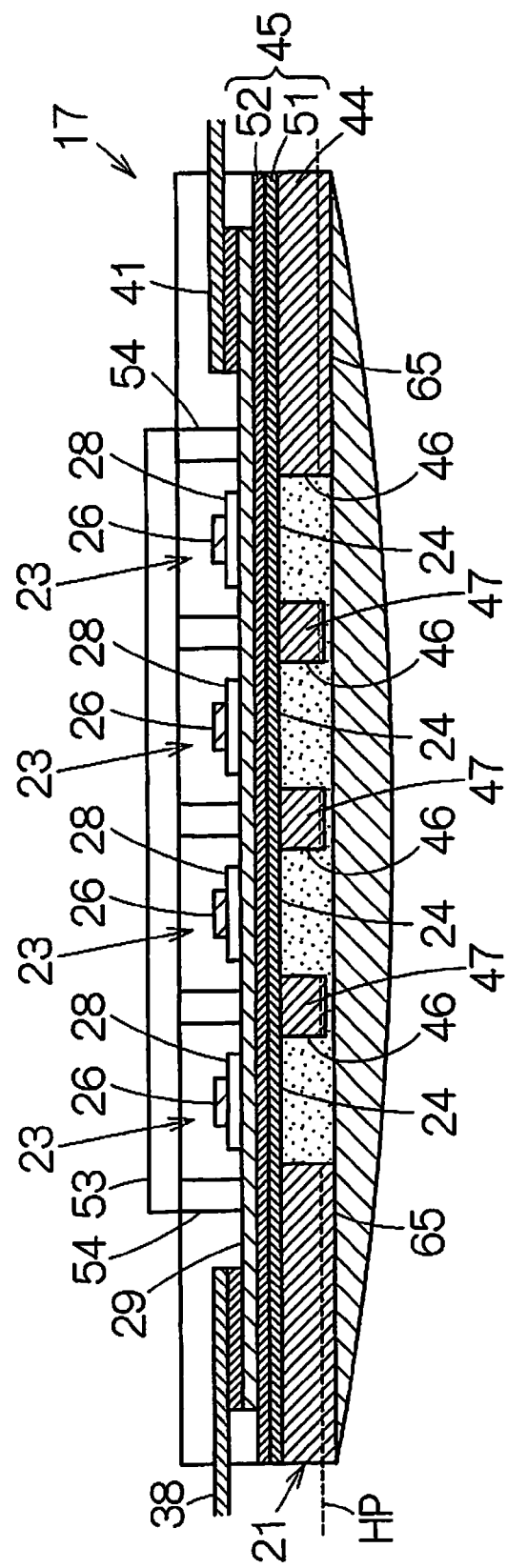
FIG. 10 is an expanded cross-sectional view corresponding to FIG. 4 according to a third embodiment of the ultrasonic device.

FIG. 10 schematically shows a cross-sectional view of the ultrasonic device 17b according to the third embodiment. In the ultrasonic device 17b, an external frame is formed at a rear surface of the substrate 44 so as to consecutively surround all of the openings 46. The external frame has a larger height than the partitioning walls 47. The acoustic lens 56 is received at the external wall. Therefore, the external frame positions the acoustic lens 56. The acoustic matching layer 55 is disposed at an interior side of the external frame. The acoustic matching layer 55 fills the openings 46. The acoustic matching layer 55 contributes to the adhesion between the acoustic lens 56 and the partitioning walls 47. Regardless of the position of the partitioning walls 47, it is possible to restrict the reduction of the adhesion area between the acoustic matching layer 55 and the acoustic lens 56 to a minimum. It is possible to stabilize the coupling of the acoustic lens 56 to the acoustic matching layer 55.

For fabrication of the ultrasonic device 17b, the rear surface 61b of the substrate 61 is subjected to etching treatment in the formation of the openings 46. At this time, it is possible to establish the height of the external frame 65 by restricting the etching at the locations corresponding to the external frame 65. For the adhesion of the acoustic lens 56, the raw material of the acoustic matching layer 55 is injected as a fluid into the openings 46. The external frame 65 blocks the raw material flowing from the opening 46. In this way, the raw material can be securely injected within all of the openings 46. The acoustic lens 56 is pressed to the external frame 65. The external frame 65 positions the acoustic lens 56.

(6) Configuration of Ultrasonic Device According to Fourth Embodiment

Figure 11:
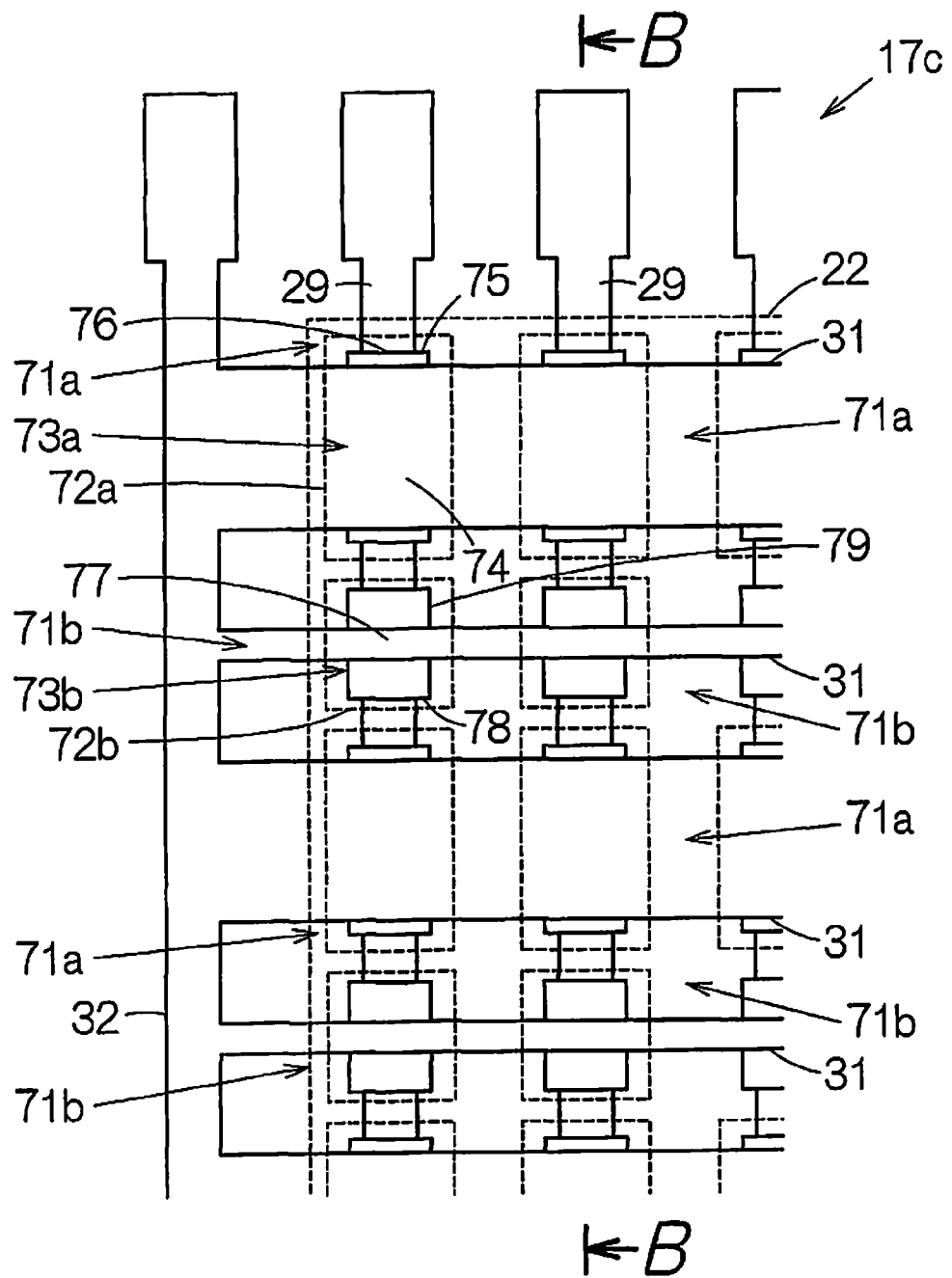
FIG. 11 is an expanded partial plan view according to a fourth embodiment of the ultrasonic device.

FIG. 11 schematically shows an expanded partial plan view of the ultrasonic device 17c according to the fourth embodiment. The element array 22 of the ultrasonic device 17c is constituted by an arrangement of first ultrasonic transducer elements (which are referred to as "first elements", hereinafter) 71a and second ultrasonic transducer elements (which are referred to as "second elements", hereinafter) 71b. Herein, the first elements 71a and the second elements 71b are alternately disposed in a row direction. However, the arrangement of the first elements 71a and the second elements 71b is not limited to this arrangement.

The first elements 71a are provided with a first vibration film 72a. The second elements 71b are provided with a second vibration film 72b. In FIG. 11, contours of the first vibration films 72a and the second vibration films 72b are shown as dotted lines in a plan view in a direction orthogonal to film surfaces of the first vibration film 72a and the second vibration film 72b (plan view in thickness direction of the substrate). A first piezoelectric element 73a is formed on the first vibration film 72a. A second piezoelectric element 73b is formed on the second vibration film 72b. In the first piezoelectric element 73a, a piezoelectric film 76 is interposed between a top electrode 74 and a bottom electrode 75. These are layered in this order. Similarly, in the second piezoelectric element 73b, a piezoelectric film 79 is interposed between a top electrode 76 and a bottom electrode 77. These are layered in this order. The first electric conductor 29 is connected commonly to the bottom electrodes 75, 78 of the first elements 71a and the second elements 71b of a single row. The second electric conductor 31 is connected commonly to the top electrodes 74, 77 of the first elements 71a or the second elements 71b of a single row. Herein, the first vibration film 72a has an area different from that of the second film 72b. The dimensions of the first vibration film 72a depend on the first resonance frequency. The dimensions of the second vibration film 72b depend on the second resonance frequency. The second resonance frequency corresponds to a harmonic wave of the first resonance frequency. However, other combinations of frequencies can be employed.

Figure 12:
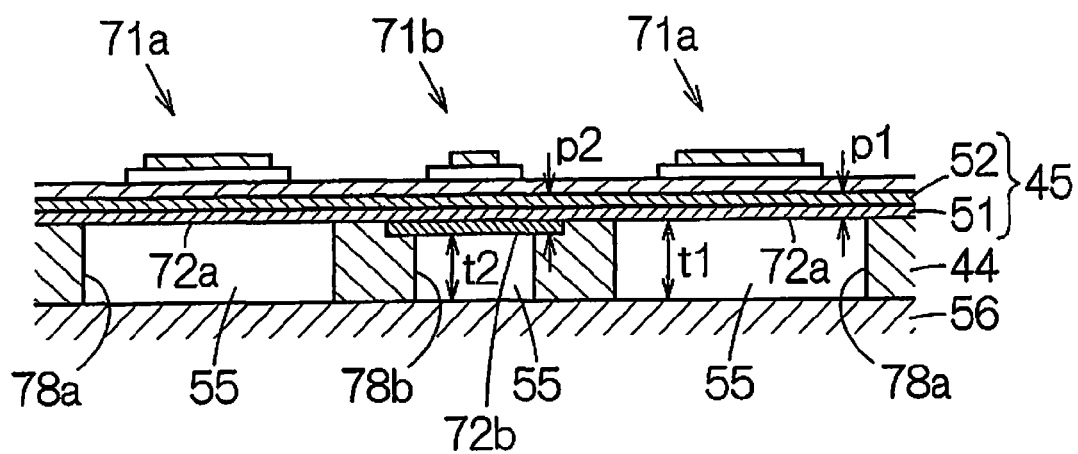
FIG. 12 is a partial cross-sectional view along B-B line in FIG. 11.

As shown in FIG. 12, the substrate 44 is provided with first openings 78a corresponding to the individual first elements 71a. The substrate 44 is provided with the second openings 78b corresponding to the individual second elements 71b. The acoustic matching layer 55 has a first thickness t1 at the first openings 78a. The acoustic matching layer 55 has a second thickness t2 at the second openings 78b. The first thickness t1 is different from the second thickness t2. The first thickness t1 is set in accordance with a first resonance frequency of the first vibration film 72a. The second thickness t2 is set in accordance with a second resonance frequency of the second vibration film 72b. In this way, the thicknesses t1, t2 of the acoustic matching layer 55 are optimized for each of the first vibration film 72a and the second vibration film 72b. Herein, for the determination of the thicknesses t1, t2 of the acoustic matching layer 55, the first vibration film 72a has a first film thickness p1, and the second vibration film 72b has a second film thickness p2. The second film thickness p2 is larger than the first film thickness p1.

For fabrication of the ultrasonic device 17c, an oxide film is formed on the surface of the substrate 61 when forming the film material 62. Silicon of the substrate 61 is oxidized to silicon oxide. In this way, the film thickness of the oxide film can be set individually for each region by controlling the oxidation amount for each region. In this way, it is possible to increase the film thickness of the oxide film for regions corresponding to the second vibration film 72b. It is possible to form the film material 62 having the first film thickness p1 and the second film thickness p2. Subsequently, the first openings 78a and the second openings 78b are formed from the rear surface of the substrate 61, allowing the silicon oxide layer 51 to function as an etching stop layer at a portion different from the rear surface of the substrate 61 in the first openings 78a and the second openings 78b. Thereby, it is possible to form the first openings 78a with a depth corresponding to the first thickness t1, and the second openings 78b with a depth corresponding to the second thickness t2. The surface of the raw material 64 injected into the first openings 78a and the second openings 78b extends in a plane. Accordingly, the fluid has different thicknesses at portions corresponding to the first vibration film 72a and portions corresponding to the second vibration film 72b. Thereby, it is possible to control the thicknesses t1, t2 of the acoustic matching layer.

On the other hand, as shown in the above embodiment, the acoustic matching layer 55 may have the same thickness at the first openings 78a and the second openings 78b. Ordinarily, the thickness of the acoustic matching 55 corresponds to an odd multiple of a quarter of a wavelength of the ultrasonic wave. If the harmonic relationship between the first resonance frequency and the second resonance frequency is satisfied, then acoustic matching can be achieved even when the same thickness is selected at the first openings 78a and the second openings 78b.

Although some embodiments of the invention have been described above in detail, those skilled in the art will readily understand that various modifications may be made without substantially departing from the new items and the effects of the invention. Therefore, such modifications are entirely included within the scope of the invention. For example, any term described at least once together with a broader or synonymous different term in the specification or the drawing may be replaced by the different term at any place in the specification or the drawings. Besides, configurations and operations of the terminal device 12, the ultrasonic probe 13, the housing 16, the display panel 15 and so forth are not limited to those described in the present embodiment, but may be modified in various ways.

The entire disclosure of Japanese Patent Application No. 2013-240276 filed on Nov. 20, 2013 is expressly incorporated by reference herein.

What is claimed is:

1. A ultrasonic device comprising:
   a substrate which has a first opening, a second opening and a wall part partitioning the first opening and the second opening,
   a first vibration film and a second vibration film which close the first opening and the second opening respectively,
   a first piezoelectric element and a second piezoelectric element which are respectively formed on surfaces of the first vibration film and the second vibration film opposite to the substrate, and
   an acoustic matching layer which is disposed within the first opening and the second opening so as to be in contact with the first vibration film and the second vibration film.

2. The ultrasonic device according to claim 1, wherein a plurality of the first openings are disposed in a row, and wherein a plurality of the second first openings are disposed in a row parallel to the arrangement of the first openings.

3. The ultrasonic device according to claim 1, wherein the wall part has a first wall part with a first height in a thickness direction of the substrate and a second wall part with a second height that is larger than the first height.

4. The ultrasonic device according to claim 3, further provided with an acoustic lens which is in contact with the second wall part and coupled to the acoustic matching layer.

5. The ultrasonic device according to claim 3, wherein the acoustic matching layer is disposed between the acoustic lens and the first wall part.

6. The ultrasonic device according to claim 1, further provided with an exterior frame which surrounds the first opening and the second opening consecutively in a plan view viewed from a thickness direction of the substrate and has a height that is larger than the wall part with respect to the thickness direction of the substrate.

7. The ultrasonic device according to claim 1, wherein the first vibration film has a first resonance frequency and the second vibration film has a second resonance frequency different from the first resonance frequency.

8. The ultrasonic device according to claim 7, wherein the acoustic matching layer has the same thickness at the first opening and the second opening.

9. The ultrasonic device according to claim 7, wherein the acoustic matching layer has different thicknesses at the first opening and the second opening.

10. A probe comprising the ultrasonic device according to claim 1, and a housing supporting the ultrasonic device.

11. An electronic device comprising the ultrasonic device according to claim 1, and a processing device which is connected to the ultrasonic device and processes an output of the ultrasonic device.

12. An ultrasonic imaging device comprising the ultrasonic device according to claim 1, and a display device which displays an image created from an output of the ultrasonic device.

\* \* \* \* \*